United States Patent [19]

Paschal

[11] Patent Number: 5,067,899
[45] Date of Patent: Nov. 26, 1991

[54] AIR-WATER DENTAL SYRINGE WITH PROTECTIVE BARRIER

[76] Inventor: Richard C. Paschal, 6608 Jocelyn Hollow Rd., Nashville, Tenn. 37205

[21] Appl. No.: 638,196

[22] Filed: Jan. 7, 1991

[51] Int. Cl.⁵ .............................................. A61G 17/02
[52] U.S. Cl. ........................................ 433/80; 433/116
[58] Field of Search ..................... 433/80, 116; 604/77, 604/268, 197, 198

[56] References Cited

U.S. PATENT DOCUMENTS

| | | | |
|---|---|---|---|
| 2,317,648 | 4/1943 | Siqveland | 433/80 |
| 2,681,408 | 6/1954 | Bronk | 433/80 X |
| 3,920,001 | 11/1975 | Edwards | 604/198 X |
| 4,611,992 | 9/1986 | Lokken | 433/80 X |
| 4,804,371 | 2/1989 | Vaillancourt | 604/198 |
| 4,900,311 | 2/1990 | Stern et al. | 604/198 |
| 4,927,416 | 5/1990 | Tomkiel | 604/198 |
| 4,975,054 | 12/1990 | Esrock | 433/80 |

FOREIGN PATENT DOCUMENTS

| | | | |
|---|---|---|---|
| 2494579 | 5/1982 | France | 433/116 |
| 14652 | 10/1933 | United Kingdom | 433/80 |

Primary Examiner—Robert P. Swiatek
Assistant Examiner—Nicholas D. Lucchesi
Attorney, Agent, or Firm—Shefte, Pinckney & Sawyer

[57] ABSTRACT

An improved air-water syringe for use by dentists and the like, the syringe including a body portion and a nozzle portion extending therefrom, with air and water passageways extending through the body portion and the nozzle portion, and with control buttons to regulate the flow of and air and water through such passageways. A protective barrier plate is mounted on the nozzle portion so that it can move relative to the nozzle portion in linear and angular directions with respect to the nozzle, whereby the protective barrier plate can be placed across the open mouth of a dental patient to prevent splashback while still permitting the syringe to be manipulated to locate the extending end of the nozzle at virtually any desired location within the oral cavity of the patient.

9 Claims, 3 Drawing Sheets

AIR-WATER DENTAL SYRINGE WITH PROTECTIVE BARRIER

BACKGROUND OF THE INVENTION

Air-water syringes have been used by dentists and qualified dental technicians in conjunction with a wide variety of dental procedures such as, for example, the routine cleaning of teeth and filling cavities.

Typically, these known air-water syringes include a body portion that is generally shaped so that it can be easily held by the dentist or dental technician during use, and a nozzle or tip that extends away from the body portion. Usually two passageways are provided, both of which extend through the body portion and the nozzle so that pressurized air and water can be introduced into such passageways, respectively, and emitted from the extending end of the nozzle portion at a predetermined flow rate. A separate control button for each of the two passageways is mounted in the body portion of the syringe so that the user can, by pressing such control button, operate a control valve in each passageway to thereby control the flow of the water and the air which is emitted from the nozzle.

In typical usage, the dentist or dental technician grasps the handle portion of the syringe, inserts the nozzle portion into the open mouth or oral cavity of the patient, and then manipulates the syringe while simultaneously operating the air or water control buttons so that jets of air and/or water (or a mist formed by depressing both buttons) can be directed, as desired, at any selected tooth or gum portions within the oral cavity for any number of purposes, such as using the water jet for flushing away blood and/or particulate matter, or using the air jet for drying a desired area within the oral cavity.

To accomplish its various functions, such as the aforesaid flushing and drying functions, the air and water must be emitted from the nozzle at a relatively high rate of flow, and, as a result, the jet of air or water tends to cause particles of water, blood, contaminants, and the like to be splashed or propagated outside of the oral cavity and in the immediate vicinity which is occupied by the dentist or dental assistant who is using the syringe. The exposure to this splashback of elements, such as blood and contaminants, creates significant health hazards for the dentist or dental technician who must have their hands and faces close to the patient's oral cavity while performing normal dental procedures, and this health hazard has increased exponentially with the increase in AIDS since the AIDS virus can be transmitted directly to the dentist or dental technician by the splashback from the mouth of an AIDS victim.

One known device for dealing with the aforesaid splashback problem is a face shield or mask that includes a translucent shield positioned over the dentist's face to act as a barrier to any splashback. While these masks do provide some protection against splashback, they have a number of disadvantages, such as being cumbersome to wear, particularly when more difficult and delicate dental procedures are being performed. Also, this shield must be cleaned at frequent intervals, and perhaps most importantly, the shield protects only the face of the user, and it provides no protection for other parts of the body (such as the arms of the user) or for surrounding surface areas where the presence of contaminates may cause additional cross-contamination to occur.

An effort had been made to deal with the aforesaid problem of splashback by providing an air barrier around the mouth of a dental patient on whom dental procedures are being performed, as disclosed in Paschal U.S. Pat. No. 4,967,320 issue Oct. 30, 1990. While this air barrier system is very effective, it requires special equipment and in a few instances, the splashback may have sufficient velocity to penetrate the air barrier. In any event, there does not appear to be any known arrangement, prior to the present invention, that can be associated directly with an air-water syringe to protect the user of such instruments from harmful splashback.

SUMMARY OF THE INVENTION

The present invention relates to a barrier plate that is associated with an otherwise conventional air-water syringe to prevent or at least significantly reduce splashback during use of the air-water syringe.

More specifically, the air-water syringe of the present invention includes a conventional body portion, a nozzle portion extending outwardly from the body portion, and at least one, and preferably two, passageways extending through the body portion and through the nozzle portion so that air and/or water delivered to such passageways can be emitted from the end of the nozzle portion, all as described above. Additionally, a protective barrier plate is provided which has dimensions that permit it to cover the open mouth of a dental patient and a mounting arrangement is provided for mounting the protective barrier plate on the nozzle portion of the air-water syringe, such mounting arrangement permitting selective relative linear movement of the protective barrier plate along the extending length of the nozzle portion and also permitting selective relative angular movement of the protective barrier plate with respect to the nozzle portion, whereby the air-water syringe can be manipulated through a wide range of positions within the mouth or oral cavity of a dental patient as described above, while the protective barrier plate remains in place covering the mouth of the dental patient to prevent or significantly reduce splashback from such oral cavity during the use of such air-water syringe.

In the preferred embodiment of the present invention, the protective barrier plate is formed from a translucent material, such as a clear plastic material, which permits the dentist or dental technician using the air-water syringe to see into the oral cavity of the patient even when the protective barrier plate is in place across the mouth of the patient, and the protective dental plate is formed with an aperture through which the nozzle portion of the air-water syringe extends. Preferably, this aperture is larger than the cross-sectional area of the nozzle portion so that there is some "play" between the protective barrier plate and the nozzle portion, whereby the nozzle portion of the air-water syringe is free to move angularly relative to the protective barrier plate during manipulation of the air-water syringe when it is in use. Also, in the preferred embodiment, a coil spring is coiled around the nozzle portion of the air-water syringe, and the coil spring extends between the body portion of the air-water syringe and the protective barrier plate so as to create a bias that urges the protective barrier plate in a direction toward the extending end of the nozzle portion of the air-water syringe, and a retaining element is placed at the extending end of such nozzle portion to prevent the protective barrier plate from being moved off of the nozzle portion. By virtue of this arrangement, the nozzle portion of the air-water syringe is free to move relatively linearly with respect to the protective barrier plate through which it extends, as well as angularly relative to the protective barrier plate, whereby, again, the air-water syringe can be manipulated through a wide range of positions to properly locate the nozzle portion of the air-water syringe at any desired location within the oral cavity of the patient.

DESCRIPTION OF THE PREFERRED EMBODIMENT

Figure 1:
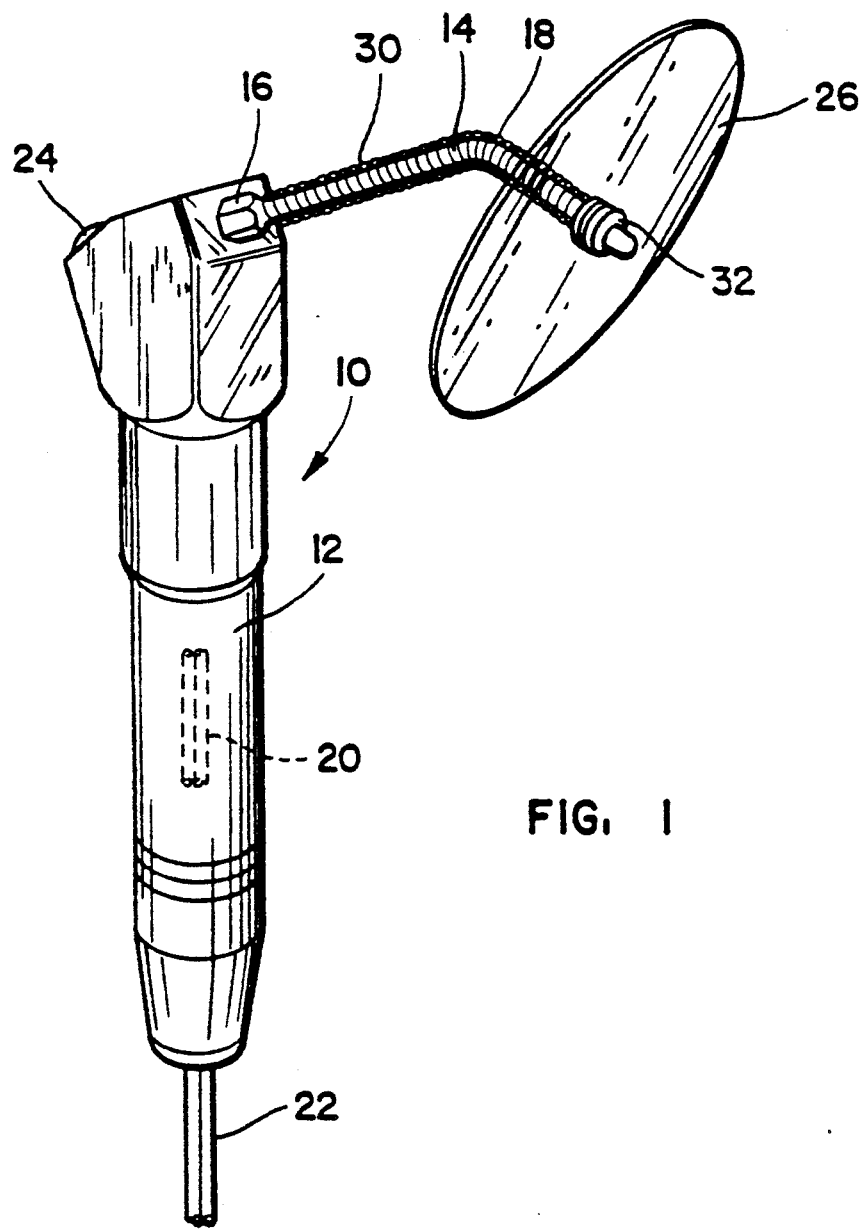
FIG. 1 is a perspective view of a typical air-water syringe which has been modified to include the protective barrier plate in accordance with the present invention.
Figure 2:
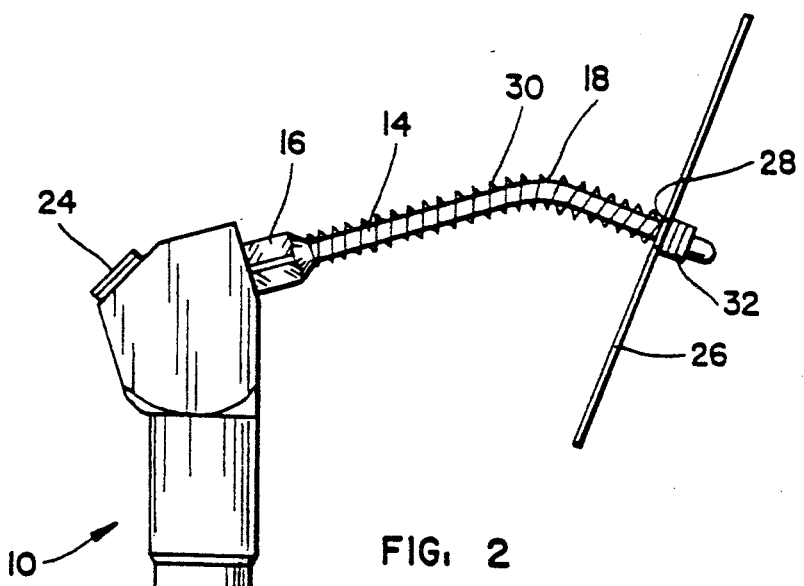
FIG. 2 is a side elevational view of the air-water syringe illustrated in FIG. 1.

Looking now in greater detail at the accompanying drawings, FIG. 1 illustrates a conventional and typical air-water syringe 10 which has been significantly modified in accordance with the present invention. The conventional syringe 10 itself includes a body portion 12 which is generally cylindrical in shape so that it can be easily held by a dentist or dental technician during use and nozzle portion 14, sometimes referred to as a "tip", which is attached to the body portion 12 by a threaded nut 16, the nozzle 14 extending outwardly from the body portion 12 and having an angle 18 formed therein. Two passageways 20, portions of which are illustrated in FIG. 1, extend upwardly through the center portion of the body portion 12 and through the nozzle 14, and the lower ends of the passageways 20 are connected to flexible tubing 22 which delivers, respectively, compressed air and water under pressure to the two passageways 20, all in a conventional manner. Also a pair of identical control buttons 24 are arranged in side-by-side relation on the back side of the body portion 12 in a conventional manner, only one such control button 24 being visible in FIGS. 2 and 4, and these control buttons 24 normally close the passageways 20 so that no air or water flows therethrough until one or the other of the control buttons 24 are pressed (usually with the thumb) by the dentist or dental technician using the syringe. When one of the passageways 20 is opened by pressing one of the control buttons 24, compressed air is emitted from the extending end of the nozzle 14, and when the other control button 24 is pressed, the other passageway 20 is opened to permit air to be emitted from the end of the nozzle 14. In some cases, both of the control buttons 24 can be pressed to create a mist. As discussed above, the pressurized air and water which are emitted from the nozzle 14 must have a sufficient flow rate to accomplish the intended purpose of the syringe, such as using the flow of water to clean and flush an area within the oral cavity where dental work is being performed, or to dry an area within the oral cavity using the air flow.

Figure 3:
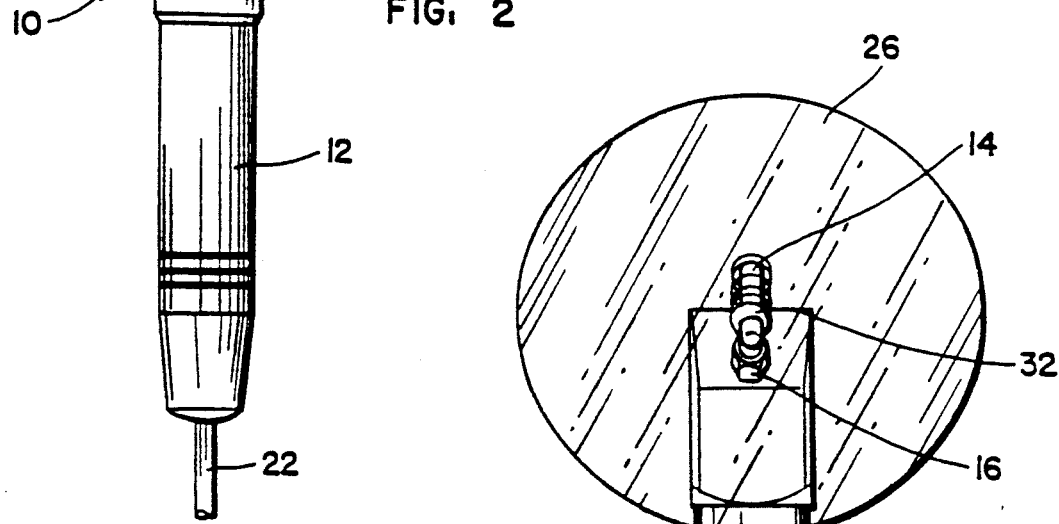
FIG. 3 is a side elevational view of the air-water syringe illustrated in FIG. 1.

In accordance with the present invention, a typical conventional air-water syringe 10 of the type described above is modified and significantly improved by mounting on the nozzle 14 a protective barrier plate 26, such barrier plate 26 being dimensioned to cover the mouth of a patient in a manner to be described presently, and the protective barrier plate 26 is preferably formed of a translucent material, such as clear plastic. The protective barrier plate 26 is formed with an aperture 28 at the approximate center thereof (see FIGS. 3 and 4) and the aperture 28 is larger than the cross-sectional area of the nozzle 14 so that selective relative angular movement of the protective barrier plate 26 with respect to the nozzle 14 is permitted. A coil spring 30 is coiled about the nozzle 14, and bears at one of its ends against the connecting nut 16 of the body portion and, at its other end, directly against the protective barrier plate 26 so as to create a bias that urges the protective barrier plate 26 in a direction towards the extending end of the nozzle 14. A retaining ring 32, preferably formed of an elastomeric material, is tightly positioned at the extending end of the nozzle 14 and is larger than the aperture 28 to provide a retaining element that prevents the protective barrier plate 26 from being pushed off the end of the nozzle 14 under the urging of the coil spring 30.

Since the aperture 28 in the protective barrier plate 26 is larger than the nozzle, angular movement of the protective barrier plate 26 relative to the nozzle 14 is permitted as described above, and the protective barrier plate 26 is also relatively movable along the extending length of the nozzle 14, both in a direction toward the body portion and against the urging of the coil spring 30, and in a direction toward the end of the nozzle 14 under the urging of the coil spring 30.

Figure 4:
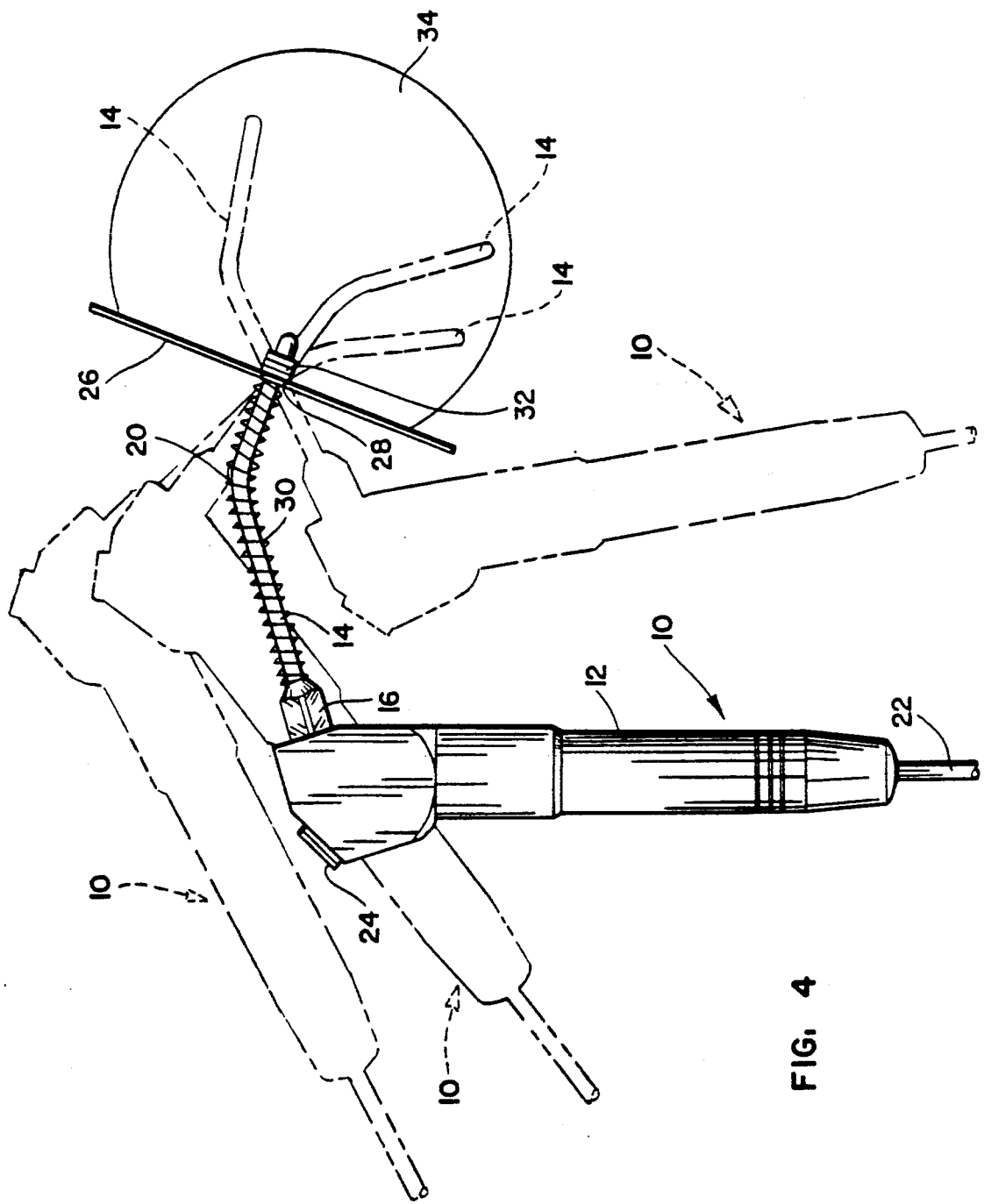
FIG. 4 is a diagrammatic view illustrating a variety of positions of the air-water syringe within the oral cavity of a dental patient.

The operation of the modified air-water syringe 10 of the present invention is diagrammatically illustrated in FIG. 4, with the open mouth or oral cavity of a dental patient being diagrammatically illustrated by the circular line 34. When it is necessary to utilize the air-water syringe 10 to emit a jet of water or air into the oral cavity 34, the air-water syringe 10 is manipulated to place the protective barrier plate 26 across the lips of the open mouth or oral cavity 34 as illustrated by the full line position of the air-water syringe 10 in FIG. 4. With the protective barrier plate 26 in place, the dentist or dental technician can further manipulate the body portion 12 of the syringe 10 to locate the extending end of the nozzle 14 at virtually any desired location within the oral cavity 34, the aforesaid relative angular movement and relative linear movement of the protective barrier plate 26 with respect to the nozzle 14 readily permitting this selective positioning of the end portion of the nozzle 14 within the oral cavity 34. Three representative positions of the nozzle 14 within the oral cavity 34 are illustrated in FIG. 4, but it is to be understood that these positions are representative only, and that the nozzle 14 may be positioned in an almost infinite number of locations within the oral cavity without disturbing the positioning of the protective barrier plate 26 across the opening of the oral cavity 34. Thus, it will be apparent from FIG. 4 that when the control buttons 24 are operated to introduce a jet of air or water, or both, into the oral cavity 34 through the extending end of the nozzle 14, any splashback or propagation of saliva, blood, foreign matter, or contaminants and the like will strike the protective barrier plate 26 and be fully contained within the oral cavity 34, rather than being propagated outside of the oral cavity and onto the dentist or dental technician, or their clothing, or any surrounding surface areas where cross-contamination can occur as discussed above.

In the preferred embodiment of the present invention, the nozzle 14 is a conventional nozzle formed of a rigid metal, but in some instances, it may be desirable to provide a disposable nozzle and protective barrier plate which can be properly discarded after each use on a new patient. When such a result is desired, the nozzle portion 14 can be made from a disposable material, such as plastic, in which case the nozzle portion 14, with the protective barrier plate 26 and the coil spring 30 mounted thereon, can be disconnected from the body portion 12 by loosening the connecting nut 16, and disposed of in its entirety.

It will therefore be readily understood by those persons skilled in the art that the present invention is susceptible of a broad utility and application. Many embodiments and adaptations of the present invention other than those herein described, as well as many variations, modifications and equivalent arrangements will be apparent from or reasonably suggested by the present invention and the foregoing description thereof, without departing from the substance or scope of the present invention. Accordingly, while the present invention has been described herein in detail in relation to its preferred embodiment, it is to be understood that this disclosure is only illustrative and exemplary of the present invention and is made merely for purposes of providing a full and enabling disclosure of the invention. The foregoing disclosure is not intended or to be construed to limit the present invention or otherwise to exclude any such other embodiments, adaptations, variations, modifications and equivalent arrangements, the present invention being limited only by the claims appended hereto and the equivalents thereof.

I claim:

1. In an air-water syringe having a body portion adapted to be hand-held, a nozzle portion connected to and extending away from said body portion, at least one passageway extending through such body portion and such nozzle portion to permit the flow of water or air therethrough, and control means for regulating the flow of water or air through said passageway, the improvement comprising:
   a) a protective barrier plate dimensioned to cover the open mouth of a dental patient; and
   b) means for mounting said protective barrier plate on said nozzle portion of said syringe said mounting means permitting selective relative linear movement of said protective barrier plate along the extending length of said nozzle portion and permitting selective relative angular movement of said protective barrier plate with respect to said nozzle portion, whereby said syringe can be manipulated through a wide range of positions within the mouth of a dental patient while said protective barrier plate is in place covering the mouth of said dental patient.

2. In an air-water syringe, the improvement as defined in claim 1 and wherein said mounting means includes an aperture formed in said protective barrier plate and extending therethrough and having a size that is at least as great as the cross-sectional area of said nozzle portion, whereby said barrier plate can move linearly along the extending length of said nozzle portion.

3. In an air-water syringe, the improvement as defined in claim 1, and wherein said aperture in said protective barrier plate is larger than said cross-sectional area of said nozzle portion whereby said protective barrier plate can move through a predetermined range of positions at which it has a different angular relationship with said nozzle portion.

4. In an air-water syringe, the improvement defined in claim 1, and wherein said protective barrier plate is generally circular in shape and is formed of a translucent material.

5. In an air-water syringe, the improvement defined in claim 1, and wherein said nozzle portion is detachable from said body portion and is made from a disposable plastic material, whereby said nozzle portion and said protective barrier plate can be removed and disposed of after use.

6. An air-water syringe that includes:
   a) a body portion adapted to be hand-held;
   b) a nozzle portion connected to and extending from said body portion;
   c) at least one passageway extending through said body portion and said nozzle portion to permit the flow of air or water therethrough;
   d) control means on said body portion for regulating the flow of water or air through said passageway;
   e) a protective barrier plate mounted on said nozzle portion and being formed of a translucent material and being dimensioned to cover the open mouth of a dental patient, and said protective barrier plate having an aperture through which said nozzle portion extends and said aperture being larger than the cross-sectional area of said nozzle portion whereby said protective barrier plate can move relatively linearly along the length of said nozzle portion and can move relatively angularly with respect to said nozzle portion;
   f) a coil spring coiled around said nozzle portion and extending between said body portion and said protective barrier plate to urge said barrier plate in a direction toward the extending end of said nozzle portion; and
   g) a retaining element positioned generally adjacent the extending end of said nozzle portion and being larger than said aperture in said protective barrier plate to prevent it from being moved off of said nozzle portion.

7. In an air-water syringe having a body portion adapted to be hand-held, a nozzle portion connected to and extending away from said body portion, at least one passageway extending through such body portion an such nozzle portion to permit the flow of water or air therethrough, and control means for regulating the flow of water or air through said passageway, the improvement comprising:
   (a) a protective barrier plate dimensioned to cover the open mouth of a dental patient; and
   (b) means for mounting said protective barrier plate on said nozzle portion of said syringe, said mounting means permitting selective relative linear movement of said protective barrier plate along the extending length of said nozzle portion and permitting selective relative angular movement of said protective barrier plate with respect to said nozzle portion, whereby said syringe can be manipulated through a wide range of positions within the mouth of a dental patient while said protective barrier plate is in place covering the mouth of said dental patient; said mounting means including biasing means for engaging said protective barrier plate to urge it toward the extending end of said nozzle portion, including retaining means for preventing said protective barrier plate from being moved off of said nozzle portion, and an aperture formed in said protective barrier plate and extending therethrough and having a size that is at least as great as the cross-sectional area of said nozzle portion.

8. In an air-water syringe, the improvement as defined in claim 7, and wherein said biasing means includes a coil spring extending along the length of said nozzle portion between said body portion of said syringe and said protective barrier plate.

9. In an air-water syringe, the improvement as defined in claim 8, and wherein said aperture in said protective barrier plate is larger than said cross-sectional area of said nozzle portion whereby said protective barrier plate can move through a predetermined range of positions at which it has a different angular relationship with said nozzle portion.

* * * * *